(12) United States Patent
Mayer

(10) Patent No.: US 6,790,624 B2
(45) Date of Patent: Sep. 14, 2004

(54) COILED-COIL MEDIATED HETERODIMERIZATION FUNCTIONAL INTERACTION TRAP

(75) Inventor: Bruce J. Mayer, Tolland, CT (US)

(73) Assignee: The University of Connecticut, Farmington, CT (US)

(*) Notice: Subject to any disclaimer, the term of this patent is extended or adjusted under 35 U.S.C. 154(b) by 238 days.

(21) Appl. No.: 09/816,756

(22) Filed: Mar. 24, 2001

(65) Prior Publication Data

US 2002/0037999 A1 Mar. 28, 2002

Related U.S. Application Data

(60) Provisional application No. 60/141,896, filed on Jun. 30, 1999.

(30) Foreign Application Priority Data

Jun. 29, 2000 (WO) ............... PCT/US00/17929

(51) Int. Cl.[7] .............................. G01N 33/53
(52) U.S. Cl. .................. 435/7.1; 435/6; 435/5; 435/4; 530/350; 536/23.4
(58) Field of Search ................. 435/7.1, 6, 5, 4; 530/350, 324; 536/23.4

(56) References Cited

U.S. PATENT DOCUMENTS 6,270,964 B1 * 8/2001 Michnick et al. .............. 435/6

FOREIGN PATENT DOCUMENTS

| WO | WO 00/07038 | 2/2000 |
|---|---|---|
| WO | WO 01/00866 | 1/2001 |

OTHER PUBLICATIONS

Tripet et al, Protein Engineering, 9, (11), 1029–1042 (1996).*
H. Hurst, Transcription Factors 1: bZIP Proteins, Protein Profile, 1995, vol. 2, Issue 2, pp. 105–168.
M. Tanaka, et al., Differential Inhibition of Signaling Pathways by Dominant–Negative SH2/SH3 Adapter Proteins, Molecular and Cellular Biology, Dec. 1995, vol. 15, No. 12, pp. 6829–6837.
R. Hodges, De Novo Design of α–helical Proteins: Basic Research to Medical Applications, Biochemistry and Cell Biology, 1996, vol. 74, No. 2, pp. 133–154.
Y. Mizukami, et al., Plant Organ Size Control: AINTEGUMENTA Regulates Growth and Cell Numbers During Organogenesis, PNAS, Jan. 18, 2000, vol. 97, No. 2, pp. 942–947.

K. Arndt, et al., Heterodimeric Coiled–Coil Peptide Pair Selected in Vivo From A Designed Library–Versus–Library Ensemble, Journal of Molecular Biology, 2000, vol. 295, pp. 627–639.
2 Hybrid System TRAFO Protocol, http://www.umanitoba, ca/faculties/medicine/biochem/gietz/2HS.html.
Mammalian Two–Hybrid Assay Kit, http://www.stratagene.com/vectors/signal_trans/mam2hyb.htm.
Display Green Two–Hybrid Kit System, http://www.displaysystems.com/Prod . . . displaygreen_two–hybrid_kit_sy.htm.
A Iivanainen, Coiled–Coil Motif in Proteins, http://www.rpi.edu/dept/chem–eng/Biotech–Enviorn/Ryan/cc.html.
Coiled–Coil Motifs are Formed, http://bmbiris.bmb.uga.edu/wampler/8010/lectures/motifs/sld018.htm.
Coiled Coil; http://www–class.unl.edu/bios201/chapter2cWEB/sid024.htm.
Some Common Protein Motifs; http://bioag.byu.edu/mcbio/130/proteinfunction/sid018.html.
The Structure of a Coiled Coil; http://bioag.byu.edu/mcbio/130/proteinfunction/sld019.html.
Coiled–Coil Structures; http://www.microbio.uab.edu/SeqCourse/08_Protein/sld043.html.
PPT Slide; http://www.microbio.uab.edu/SeqCourse/08_Protein/sld045.html.
New Twists in Globs and Zippers; http://www.psc.edu/science/Brooks96/brooks96/html, pp. 1–3.
Predition of Coiled Coils from Protein Sequences; http://www.york.ac.uk/depts/biol/units/coils/coilcoil.html.
Structural Classification of Proteins, Class: Coiled Coil Proteins; http://www.edu.au/scop/data/scop.1.008.html.
GAL4 (Residues 1–65); ftp://www.expasy.ch/databases/swiss–3dimage/IMAGES/JPEG/1D66_gal4_1.jpg.
Motifs; http://mytilene.ucdavis.edu/~smith . . . ir/Protein_Structure_II/sld017.html; Slides 2, and 17–29.
Posttranslational Modifications; http://mytilene.ucdavis.edu/~smith . . . r/Protein_Structure_III/sld001.html; Slides 1–6, 10 and 26.
Influenza Virus Haemagglutinin, http://www.rpi.edu/dept/chem–eng/Biotech–Enviorn/Ryan/cc.html, pp. 4–5.

* cited by examiner

Primary Examiner—T. D. Wessendorf
(74) Attorney, Agent, or Firm—McCarter & English LLP

(57) ABSTRACT

Fusion proteins containing coiled-coil heterodimerization domains substituted for modular protein binding domains useful for validating functionally relevant protein-protein interactions, directing enzymes to specific substrates, and screening fusion libraries for functionally important interaction partners.

2 Claims, 3 Drawing Sheets

SEQ ID No:1

HA epitope tag

ACC ATG TAC CCA TAC GAT GTT CCG GAT TAC GGA TCT ACC ATG ACT GTG GCG CAA CTG GAG GAA
thr met tyr pro tyr asp val pro asp tyr ala gly ser thr met thr val ala gln leu glu glu AAG GTG AAA ACC CTT CGT GCT CAG AAT TAT GAA CTT AAG TCT CGT GTG CAG CGC TTG CGT GAG CAG
lys val lys thr leu arg ala gln asn tyr glu leu lys ser arg val gln arg leu arg glu gln GTT GCC CAG CTT GGA GGA GGA TCC --- ---
val ala gln leu gly gly gly ser

FIG. 1

SEQ ID No:2

```
                Myc epitope tag
ACC ATG GAG CAA AAG CTC ATT TCT GAA GAG GAC TTG AAT GAA GGA TCT ACC ATG TCC GTT GAC GAA
thr met glu gln lys leu ile ser glu glu asp leu asn glu gly ser thr met ser val asp glu CTG CAG GCT GAG GTT GAC GAG GAC GAG AAT TAC GCT CTG AAG ACC AAG GTT GCG CAG CTG
leu gln ala glu val asp glu asp glu asn tyr ala leu lys thr lys val ala gln leu CGT AAA AAG GTG GAA AAG CTG GGA GGA TCC --- ---
arg lys lys val glu lys leu gly gly gly ser
```

COILED-COIL MEDIATED HETERODIMERIZATION FUNCTIONAL INTERACTION TRAP

RELATED APPLICATION(S)

This application claims the benefit of U.S. Provisional Application No. 60/141,896, filed Jun. 30, 1999 and PCT Application No. PCT/US00/7929, filed Jun. 29, 2000 entitled "Fusion Protein and Uses Thereof", and the entire teachings of each application are incorporated herein by reference.

FIELD OF THE INVENTION

The present invention is directed to fusion proteins having high affinity coiled-coil heterodimerization domains in place of a modular protein binding domain and the use in an assay system for (1) validating that a protein-protein interaction causes a specific biological activity, (2) identifying target molecules capable of affecting those interactions and (3) identifying the biological activities involved in such interactions. In particular, the present invention is directed to fusion proteins containing an exogenously introduced zipper.

BACKGROUND OF THE INVENTION

Many critical cell processes are regulated by specific protein-protein interactions. These interactions can cause signal transduction or processes governing whether a cell will proliferate, differentiate, die, adhere, migrate or otherwise respond to its environment. Protein-protein interactions may entail, for example, between a receptor and its target ligand (such as $VEGF_{165}$ Receptor—Neuropilin-1 complexes) as well as intracellular interactions (such as adaptor-kinase complexes). If one could identify in vivo binding partners, the manner in which proteins exert their activity might be discerned. If the activity of the protein is relevant to disease, then the binding proteins might also be novel targets for drug discovery. Unfortunately, in many cases a protein binds not one, but many other proteins with similar affinity. It is often therefore difficult or impossible to ascribe any functional significance to any particular interaction. This is a major stumbling block to the ability to understand the precise inner workings of the cell.

Protein-protein interactions typically involve the modular protein binding domains (MPBD) of one protein, which are regions of about 60 to 200 amino acids, and the corresponding binding site of the second protein. Examples of such domains are SH2 (src homology 2), SH3 (src Homology 3) and PTB. These domains typically bind to linear peptide epitopes of about 4–10 amino acid residues on their binding partners. MPBDs are present in a wide variety of functionally distinct proteins. For example, the SH2 domain, which binds to phosphorylated tyrosine residues, is contained in many different signaling proteins and their binding sites are found on a wide range of activated growth factors, e.g. epidermal growth factor, platelet-derived growth factor, fibroblast growth factor, etc.

Despite the fact that numerous MPBDs and their corresponding binding sites (BSs) have been identified, these discoveries themselves do not shed light on whether a pair of proteins actually interact in vivo and whether that interaction is important for biological activity. This is because the binding interaction between MPBDs and their corresponding binding sites is not highly specific, but is only partially specific. Consequently, one protein can bind with several to hundreds of other proteins with virtually the same affinity. This lack of specificity has created a fundamental stumbling block. For example, if a single SH3 domain can bind with virtually identical affinity to tens or even hundreds of different proteins in the cell, and a single SH3 binding site can combine with tens or hundreds of different SH3 domains, which of these hundreds of potential protein complexes actually results in a specific in vivo function?

The determination of the specific pair of protein-protein interactions that results in a biologically activity is typically done indirectly, e.g., by preventing the specific interaction between the proteins to determine if preventing binding of a set of proteins eliminates a function. The latter could be performed, for example, by altering the MPBD and/or BS to prevent binding. However, such an alteration will also prevent binding with other proteins. Therefore that method does not definitively confirm that the specific biomolecular protein complex under investigation actually interacts in the cell to result in the function eliminated. For example, protein A may interact with protein 55 at one point in a pathway, whereas protein 5 interacts with protein D at a different point in the pathway. Thus, by altering the binding sites of proteins A and 5, the function could be lost without the two proteins having to interact directly with each other.

There also exists a method for studying protein-protein interactions wherein proteins are attached to one another through bifunctional molecules. In this approach, proteins are synthetised as fusions which bind a small-molecule drug, and the small-molecule drug is added. This method works well for some applications, but the protein fusion partners tend to be quite bulky and the affinities of interaction somewhat low. The dimerization drugs may also only be available by licensing from companies.

The predominant system used today for studying protein-protein interactions is the two-hybrid assay system. In this method a selectable output such as growth on a selected media, or metabolism of colorimetric substrates is dependent on reconstituting a protein-protein interaction with a "bait" protein. Such a system is limited, in that the selectable biological output is fixed by the experimental system and proteins are screened for their ability to bind to the target (bait) protein. Further, one is typically trying to reconstitute function in a foreign system, e.g., yeast, as opposed to a mammalian cell system. It would be desirable to have a system that forces interactions between the proteins and looks at their functional consequences. It would also be desirable to have a system that more closely resembles the actual cellular microenvironment where the protein-protein interactions occurs.

In co-pending PCT Application No. PCT/US00/17929, filed Jun. 29, 2000 and entitled "Fusion Protein and Uses Thereof," the present inventor discloses a Functional Interaction Trap("FIT") system which depends on a protein binding interface consisting of two engineered protein segments. One fusion protein comprises a protein containing a modular protein binding domain (MPBD), wherein the MPBD is substituted by a single chain antibody. The MPBD may be selected from the group of domains consisting of src homology 2 (SH2), src homology 3 (SH3) phosphotyrosine binding (PTB), WW, PDZ, 14.3.3, WD40, EH, Lim, etc. The second fusion protein comprises a protein containing a binding site that binds to a modular protein binding domain MPBD, wherein at least one linear epitope that binds to the MPBD within the binding site is substituted by an antigenic epitope of 6–20 amino acids that binds to the single chain antibody that has been substituted for the MPBD. Preferably, the second fusion protein contains multiple copies of the epitope. For example, 2–20, more preferably 3–15, still more preferably 4–10 copies of the epitope. Nucleic acid sequences encoding these fusion proteins can be prepared by known techniques. Preferably these sequences (e.g., genes) are contained in vectors and are operably linked to a promoter. These vectors can be used to transform a cell. When the protein fused to the ScFv interacts with the second protein fused to the epitope the two proteins bind to each other. Such interaction can only occur if both modified proteins are expressed in the same cell. The unique biological consequences of the interaction can be assessed to provide information previously unaccessible by prior art techniques.

The antibody FIT technique is not always optimal in that the specificity of the reaction between the particular ScFv and epitope may permit in the reducing environment of the cytosol reactivity with other unintended proteins. The intracellular environment does not favor the disulfide bonds that normally stabilize the structure of the antibody in the extracellular environment. In the intracellular environment ScFvs may be susceptible to unfolding and thus may be unstable and insoluble. It would be desirable to have a protein that can still perform its native functions, but can bind with even higher affinity to its putative partner than presently available. It would also be useful to have a method to replace the relatively nonspecific interactions between two proteins with a highly specific interaction, thereby allowing the two proteins of interest to directly interact without concern for competing interactions with other proteins in the cell.

SUMMARY OF THE INVENTION

It has been discovered that novel fusion proteins having high affinity coiled-coil heterodimerization domains (Kd of heterodimerization interaction less than, or equal to, 30 nM, more preferably less than, or equal to, 28 nM, and more preferably less than, or equal to, 26 nM) in place of a modular protein binding domain can be used in assays to identify the effect of protein-protein interactions.

Particularly preferred high affinity coiled-coil heterodimerization domains of the present invention are the WIN-ZIP coiled-coil heterodimerization leucine zippers, such as those described by Michnik and colleagues (See, e.g., Arndt, K. M., J. N. Pelletier, K. M. Muller, T. Alber, S. W. Michnick and A. Pluckthun, A heterodimeric coiled-coil peptide pair selected in vivo from a designed library-versus-library ensemble, *J Mol. Biol.* 295:627–630 (2000).

One fusion protein of the present invention comprises a protein containing a modular protein binding domain (MPBD), wherein the MPBD is substituted by a WIN -ZIP A1 segment. Preferably, the MPBD is selected from the group of domains consisting of src homology 2 (SH2), src homology 3 (SH3) phosphotyrosine binding (PTB), WW, PDZ, 14.3.3, WD40, EH, Lim, etc. For example, such a protein may be a tyrosine kinase. A second fusion protein comprises a protein containing a binding site that binds to a modular protein binding domain MPBD, wherein at least one linear epitope that binds to the MPBD within the binding site is substituted by a WIN-ZIP B1 segment.

It is believed when two proteins are expressed in transiently transfected mammalian cells that if one is a WIN-ZIP A1 fusion, and the other WIN-ZIP B1 fusion, the two proteins will specifically bind each other and stably co-precipitate from cell lysates in a ratio close to 1:1 by forming stable heterodimerization coiled-coil structures. The present inventor has found that when the WIN-ZIP A1 fusion is the Src tyrosine kinase, a co-expressed WIN-ZIP B1 fusion is specifically phosphorylated on typrosine by Src (but is not phosphorylated to nearly the same extent if either of the two proteins does not bear the WIN-ZIP segment). Thus this system, may be used to induce the highly specific phosphorylation of particular substrates by kinases of interest, at least in the cases where the kinase is known to require substrate interaction domains to efficiently phosphorylate its substrates (this is the case for all non-receptor tyrosine kinases, cyclin-dependent kinases, MAP kinases, etc.). No other system currently available allows the assay in vivo of the consequences of phosphorylation of a single substrate of interest.

As would be understood by one of ordinary skill in the art, the FIT WIN-ZIP approach of the present invention permits the specific binding of two proteins that normally would not interact in the cell, as well as those proteins that would normally interact. It can also be used to direct an enzyme to act specifically on a single substrate protein of choice. The availability of this interface permits one to easily test the functional consequences of binding for specific pairs of proteins, and to screen large libraries of proteins for those whose interaction with a protein of choice gives some biological activity of interest.

Nucleic acid sequences encoding these fusion proteins can be prepared by known techniques. Preferably these sequences (e.g., genes) are contained in vectors and are operably linked to a promoter. These vectors can be used to transform a cell. These transformed cells can be used to identify the function of a protein-protein interaction, to identify a particular protein involved in an interaction and to study the specific effect of specific functional domains.

In one embodiment there is an assay for determining the activity of a protein-protein interaction, comprising:

(a) transforming a cell with a first vector containing a gene encoding a first fusion protein comprising MPBD and an exogenously introduced coiled-coil dimerization domain, and with a second vector, wherein said second vector contains a gene encoding a second fusion protein comprising a binding site for the MPBD and an exogenously introduced second coiled-coil dimerization domain interactive with the first coiled-coil dimerization domain;

(b) culturing the transformed cell;

(c) and comparing the activity to a base line control; and (d) measuring changes in activity to determine the activity caused by that protein-protein interaction.

Preferably, the cell used does not express the protein containing the MPBD of the fusion protein encoded by the gene contained in the transforming vector or the effect of the interaction is dominant or assayed in a way that does not depend on the lack of the wild-type counterpart of the engineered gene. The control can be an untransformed cell, or more preferably cells transformed with each of the modified fusion proteins, alone, but not together. By this latter way, one can determine the effect of expression of each of the proteins on the cell and determine what effects are dependent on the interaction of the two proteins.

Full-length cDNAs fused to sequences encoding coiled-coil heterodimerization segments may be used in FIT screens. The coiled-coil heterodimerization segments such as WIN-ZIP are short enough that it is possible to synthesize them in vitro and couple them to various chemical groups (fluorophores, reactive groups, inhibitors, membrane-transit domains, etc.) for in vitro biochemical studies on purified enzymes or studies in tissue culture cells.

BRIEF DESCRIPTION OF THE FIGURES

FIG. 1 shows a nucleotide sequence (SEQ ID NO: 1) useful for practicing the present invention, wherein a Kozak translation start site is followed by an HA-epitope, followed by a WIN-ZIP-A1 synthetic amphiphatic helix, followed by an in-frame BamHI cloning site which may be may be followed by the sequence of a protein of choice.

FIG. 2 shows a nucleotide sequence (SEQ ID NO: 2) useful for practicing the present invention, wherein a Kozak translation start site is followed by an Myc-epitope, followed by a WIN-ZIP-B1 synthetic amphiphatic helix, followed by an in-frame BamHI cloning site which may be followed by the sequence of a protein of choice.

DETAILED DESCRIPTION OF THE INVENTION

Figure 3A:
FIGS. 3A–3C are electrophoresis gels of whole cell lysates probed with anti-HA (FIG. 3A) and anti-Myc immunoprecitates probed with anti-Myc (FIG. 3B) or anti-Ptyr (FIG. 3C).

We have now discovered that by creating a first fusion protein having a first coiled-coil heterodimerization domain and a second fusion protein having a second coiled-coil heterodimerization domain interactive with the first coiled-coil heterodimerization domain, so as to form a coiled-coil heterodimer with the same, one can obtain high affinity protein-protein binding interactions, to the exclusion of competing reactions. The high affinity protein-protein binding interactions can be used to determine the phenotypic responses of cells to protein interactions. The coiled-coil heterodimerization fusions can be tailored so that one does not change, or minimally changes, the conformation of the fusion protein in comparison to the wild type conformation. Consequently, the concerns about competition resulting in different interactions between one of the proteins and an unknown protein, or change that result in a functionally inactive protein, are greatly reduced.

Much of the recent progress in understanding the molecular basis of signal transduction, growth control, and cancer has been based on the analysis of protein-protein interactions and their consequences. There are frustrating limitations to this type of analysis, however, arising from the fact that the signaling machinery is based on networks of overlapping interactions. The problem can be illustrated by considering a common protein-interaction module such as the SH3 domain. Often it can be shown that mutation of either the domain or a potential binding site affects the activity of a protein containing it, or conversely overexpression of the isolated domain or binding site itself has phenotypic consequences in the cell. The implication of such results is that some cellular protein interacts with the SH3 domain or binding site, and that interaction has important consequences. The problem in the art, however, is how to identify the crucial binding protein.

While a variety of tools are available that allow the isolation of binding partners, modular protein interaction domains almost always bind not a single protein, but many proteins with similar affinity. Therefore it cannot be said based on such isolation of binding partners that the binding proteins are actually involved in a biological activity of interest. To address this need, the present inventor has developed a novel proteomic method that termed the "Functional Interaction Trap," or "FIT."

According to the teachings of the present invention, one can now assay for the specific effect that occurs when protein A binds with protein B. This contrasts with previous methodologies where in attempting to determine the effect of such an interaction, negative effects were discerned, i.e. deleting the MPBD of protein A and the binding site protein of B. Such an assay could not clearly establish that protein A actually interacts with protein B. For example, assume protein A interacts with protein D and protein B interacts with protein F and that the interaction is in the same biological pathway. Deletions in the MPBD in protein A would prevent binding with protein E, which could result in a loss of activity. Similarly a deletion in the binding site of protein B would prevent its ability to bind with protein E, thereby also resulting in a loss of activity. However, by looking at the change in function occurring from the above-mentioned deletions, one would not know that protein A and protein B did not actually interact with each other.

The FIT assay of the present invention depends on a protein binding interface consisting of two engineered protein segments, coiled-coil heterodimerization segments, each fused in-frame to one of two proteins. Only when both modified proteins are expressed in the same cell will the two proteins bind each other, and the unique biological consequences of the interaction be assessed. Since the fusion proteins of the present invention act positively, namely by actually interacting, one can look for generation of a function instead of loss of function for the complex.

In a preferred embodiment of the present invention, a coiled-coil dimerization system based on the WIN-ZIP synthetic zippers first described by Michnick and colleagues are employed (See, Arndt, K. M., J. N. Pelletier, K. M. Muller, T. Alber, S. W. Michnick, and A. Pluckthun. A heterodimeric coiled-coil peptide pair selected in vivo form a designed library-versus-library ensemble, *J. Mol. Biol.* 295:627–639 (2000). These zippers have been found by the present inventor to work in cells at an affinity comparable to those of biologically important interactions.

As would be understood by one of ordinary skill in the art, numerous constructed eukaryotic expression vectors may be found useful in the practice of the present invention. Two exemplary DNA sequences that may be inserted into such vectors are set forth below:

a. A Kozak translation start site, followed by an HA-epitope, followed by the WIN-ZIP-A1 synthetic amphipathic helix [1], followed by an in-frame BamHI cloning site, followed by the coding sequence for a protein of choice, as shown in FIG. 1.

b. A Kozak translation start site, followed by a Myc-epitope, followed by the WIN-ZIP-B 1 synthetic amphipathic helix, followed by an in-frame BamHI cloning site, followed by the coding sequence for a protein of choice, as shown in FIG. 2

Such DNA sequences may be inserted into any vector of choice, including yeast expression vectors, or retroviral vectors for the infection of mammalian cells. A advantageous expression vector is pEBB (Tanaka, M. R. Gupta, and B. J. Mayer, Differential inhibition of signaling pathways by dominant-negative SH2/SH3 adapter proteins, *Mol. Cell. Biol.* 15:6829–6837 (1995)). Furthermore, different epitope tags can be appended to the N-terminus. Also the WIN-ZIP segments could be constructed into FIT-compatible vectors such that they will be fused to the C-terminus (instead of the N-terminus) of the resulting protein, along with appropriate epitope tags.

One can transform any cell with vectors containing genes encoding the fusion proteins of the present invention. One can then compare these fusion protein transformed cells with a base line of a control of the same cell to see the differences that occur in these cells. Preferably, the genes are placed under the control of a promoter that results in high levels of expression of the fusion protein. Other instances and sequences that result in enhancing expression also can be used. For example, a HIV TAR element upstream and operably-linked to the gene and a sequence encoding the HIV tat will result in increasing expression by factors of $10^3$. Other such sequences are known.

Preferably, one can use a cell line where at least one of the native proteins being studied is not expressed or minimally expressed. Such cells may occur naturally or may be engineered. These cells are referred to herein as "knockout" cells. Knockout cells are well known in the art. Many knock out cells are commercially available from a variety of different manufacturers. If one desires, one can reduce the level of endogenous gene expression of a particular protein in a cell i.e. knock out the gene by using anti-sense, or ribozyme approaches to inhibit or prevent translation of the protein's mRNA transcripts, preferably targeting the endogenous promoter; intracellular targeting of antibodies to the protein to prevent its expression, triple helix approaches to inhibit transcription of the gene, targeted homologous recombination to inactivate or knock out the gene or the endogenous promoter. Preferably one would knock out the endogenous promoter. See Wagner, R. *Nature,* 3782:333–335 (1994), Saver et al., *Science,* 247:1222–1225 (1990), Helene, C., *Anti Cancer Drug Des.,* 6:569–84 (1991); Helene, C. et al., *Ann. NY Acad. Sci.,* 660:27–36 (1992); Marasco, W. (U.S. Pat. No. 5,965,374). Alternatively, as mentioned above, there are many instances where the protein of interest is not being expressed at a particular time in a cell's cycle or in a particular type of cell. Such cells can readily be screened for, for example, by looking for presence of the transcript of the protein using standard detection means including differential display techniques.

Additionally, in many cases the phenotype will be dominant (such as seen with oncogenes, viral proteins, etc), and the activity caused by the protein-protein interaction will be seen in cells which still express the two proteins.

In a preferred embodiment the coiled-coil heterodimer is a zipper, preferably a synthetic leucine zipper. In a preferred embodiment, the zipper is formed by two WIN-ZIP synthetic amphiphatic segments. In a particularly preferred embodiment, the one fusion protein comprises a WIN-ZIP-A1 synthetic amphiphatic segment, and the other fusion protein comprises a WIN-ZIP-B1 synthetic amphiphatic segment. Kd of the heterodimer interaction is preferred to be less than, or equal to, 30 nM, more preferably less than, or equal to, 28 nM, and yet more preferably less than, or equal to, 26 riM. The WIN-ZIP segments preferably interact with each other in a manner such that near stoichiometric levels of tagged proteins are found to co-precipitate.

In creating one of the fusion proteins of the present invention, the MPBD of the protein is replaced with a WIN-ZIP-A1 synthetic amphiphatic segment. As such segment contains a short stretch of amino acids, it readily can be substituted for the MPBD without significantly affecting the conformation of the protein.

The following example is illustrative of the ways one can look at a protein-protein interaction.

The role of adaptor proteins is to modulate the localization, local concentration and binding partners of the proteins with which they interact. The fundamental problem with fully understanding their activity is that they contain MPBD, namely, SH2 and SH3 domains—that are promiscuous in their binding activities (i.e. are not specific). Ab1 is a kinase that has a corresponding binding site that is believed to form a complex with an adaptor protein. Yet, because of the mutual lack of specificity for specific adaptor-kinase complexes it is difficult to assess which of the many adaptors that Ab1 can bind to in vivo is responsible for the activity of interest. This is because Ab1 can bind to the SH3 domains of a range of adaptors. Similarly, the multiple adaptors that contain the SH3 domains that can bind to the Ab1-adaptor-binding site may also bind to numerous proteins other than Ab1. By the present invention, the interaction interface between the SH3 domain of the adaptor and their binding sites on Ab1 (the kinase) can be replaced by a synthetic high affinity, specific interaction, i.e., a WIN-ZIP synthetic leucine zipper. Preferably the main SH3 domain in an adaptor is replaced with a WIN-ZIP synthetic coiled-coil heterodimerization domain (such as WIN-ZIP-A1) and at least one of the corresponding WIN-ZIP synthetic coiled-coil heterodimerization domains (such as WIN-ZIP-B 1) is inserted into an Ab1 molecule in which the authentic adaptor binding sites have been ablated. This results in only one interaction. A plurality of synthetic coiled-coil heterodimerization domains may be employed in the fusion protein.

In another embodiment, the fusion proteins containing the coiled-coil heterodimerization domains can be used to bring specified functional groups into close proximity. Various functional domains for a wide range of proteins are well known in the art. Other functional domains can readily be determined by known means such as the deletion mutant technique. Virtually any arrangement of functional domains desired can be prepared.

The novel fusion proteins of the present invention can be used in a number of ways. For example, in an assay to determine the biological activity of a specific protein-protein pair. The fusion proteins of the present invention may also be used for:

1. testing the significance of interaction between a specific pair of proteins in vitro, in cultured cells, or in genetically modified animals.
2. testing which, of a series of potential protein interaction partners for a protein of interest identified by a prior screening assay, such as the yeast two-hybrid assay, is responsible for biological activity of interest in vitro, in cultured cells, or in genetically modified animals;
3. identifying binding partners for proteins of interest (including enzyme substrate pairs) whose interactions results in biological activity of interest in cells (e.g.; screening libraries expressing protein modified with the WIN-ZIP synthetic dimerization domain in cells expressing a protein of interest fused to the second WIN-ZIP domain).
4. improving enzyme-substrate interactions by increasing the proximity of the enzyme to the substrate.
5. identifying proteins that, when associated with another protein-based functional group by WIN-ZIP-mediated zipper interaction, leads to biological activity of interest (Functional groups include subcellular targeting signals, oligomerization domains, engineered constructs permitting induced aggregation, etc. These can include functional groups fused to a WIN-ZIP synthetic coiled-coil heterodimerization segments, screened with libraries of proteins containing the corresponding WIN-ZIP synthetic coiled-coil heterodimerization segment); and
6. appending functional groups (such as chemical groups, fluorescent dyes, etc.) to protein or proteins of interest in cells or in vitro (Such functional groups can be covalently coupled to synthetic peptide and proteins of interest modified with the WIN-ZIP synthetic coiled-coil heterodimerization segment by known means).

More specifically, one can create ectopic SH2 domains. For example one method of bringing novel functional domains into proximity with a target protein is by using the N-terminal SH2 of GAP, which is known to have a high affinity for phosphorylated p62dok. Thus, one can determine if Ab1 facilitates phosphorylation (measurable biological output) of p62dok (second known protein). Adaptors bind Ab1 via their SH3 domains, and provide an SH2 domain to the kinase, which may be useful for phosphorylation of some proteins by Ab1. Using this system novel SH2 domains such as that of GAP can be brought into close proximity to Ab1. In this way, one can, for example, look at the effect of the specific phosphorylation of a single protein by a kinase. While kinases can have profound biological effects, it is not clear what the consequences of phosphorylation of any single substrate might be. For example, Ab1 can transform cells, but the specific substrates essential for this product are not known. However, with Ab1 oncogenic transformation requires a functional SH2 domain [Mayer, B. J., et al., *Mol. Cell Biol.* 12:609–610 (1992). Accordingly, if the SH2 domain of Ab1 is replaced with a WIN-ZIP coiled-coil heterodimerization domain, the mutant will not transform cells or phosphorylate substrates efficiently. Then, using at least one copy of the corresponding Win-ZIP coiled-coil heterodimerization domain, one can direct a protein to bind to and be phosphorylated by Ab1. In this manner, one can evaluate the biological consequences of phosphorylation of the specific protein, or to isolate and identify from a library, those substrates (proteins) displaying a desired property (e.g., transformation) when phosphorylated. Other proteins involved in phosphorylation in addition to Ab1 can readily be used.

Similarly, one can create specific targeting domains such as the focal adhesion target (FAT) region of FAK. This allows the testing of effects of relocalization (or targeting) in the absence of the increased processitivity conferred by an SH2 domain.

In order to circumvent the lack of specificity of SH2-phosphopeptide interactions, e.g. an SH2/SH3 adaptor, for instance the Nck SH3 domains can be directly targeted to subcellular locations known to directly harbor Nck SH2-binding sites, allowing for the experimental mimicking of signal-induced creation of localized binding sites for the Nck SH2 domain without relocalizing other SH2-containing proteins. By appropriate mutagenesis one can alter the local concentration of Nck SH3 domains on the membrane, mimic clustering of the tyrosine phosphorylated sites involved in normal stimuli such as TCR engagement or receptor clustering e.g. Eph receptor. Accordingly one can replace any MPBD, such as the SH3 domain or domains of for example Nck with the WIN-ZIP coiled-coil heterodimerization domain.

Consequently, one can use the fusion WIN-ZIP coiled-coil heterodimerization zipper combinations described here as a screening technology to validate suspected interactions and to identify functionally important interactions.

Even if one can not readily test protein pairs in a cellular system to ensure that it is the binding between these two proteins that is responsible for a particular function, one can look at such prospective native proteins in any system and tag them and use deletion mutants to determine which are the most important MPBDs and binding sites in those two proteins. This approach can be adapted for studying a wide range of protein-protein interactions. For example, the interaction of cellular proteins with certain viral proteins can have many undesired affects. For instance it is known that the HIV Nef protein interacts with cellular protein(s) to reduce immune function. However the interaction of Nef with particular protein(s), where binding has functional consequences, are not currently known because of the lack of specificity in protein binding. One could take a Nef protein, insert a first WIN-ZIP coiled-coil heterodimerization domain, and attach the corresponding WIN-ZIP coiled-coil heterodimerization domain (so as to form a zipper) to a library of proteins. Thereafter, one can transform cells with the Nef protein and the library of different proteins. In this manner one can rapidly identify, the protein that interacts with Nef to result in the function being sought. Once the particular protein is identified, which can be done by standard techniques, e.g., by downregulation of immune function by Nef, one can look for compounds that interact with this protein. This permits a rational drug design.

Typically, one will use a library of nucleic acid sequences encoding the desired proteins. These nucleic acid libraries will be used to create a vector library that can be used to transform the desired cells.

Alternatively, fusing the first WIN-ZIP coiled-coil heterodimerization domain to various dominant targeting sequences or other functional domains e.g., membrane localization, nuclear localization, focal adhesions or cross-linkable membrane domains, allows for screening of libraries of corresponding second WIN-ZIP coiled-coil heterodimerization domain target fusion proteins. One can then screen for a specific biological output in specific cellular compartments. Thereafter, one can use standard techniques to identify the protein complex.

Those of ordinary skill in the art will recognize that a large variety of possible moieties can be coupled to the WIN-ZIP coiled-coil heterodimerization segments or to other coiled-coil heterodimerization molecules of the invention for ease in subsequently identifying a functionally important complex. This is particularly useful when one is using a library of proteins to identify the unknown protein that interacts with a known protein. See, for example, "Conjugate Vaccines", Contributions to Microbiology and Immunology, J. M. Cruse and R. E. Lewis, Jr (eds), Carger Press, New York, (1989), the entire contents of which are incorporated herein by reference. In some instances, one would use genetic engineering to couple moieties.

Coupling may be accomplished by any chemical reaction. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodimides, succinimide esters, diisocyanates, glutaraldehydes, diazobenzenes and hexamethylene diamines. 'This listing is not intended to be exhaustive of the various classes of coupling agents known in the art but, rather, is exemplary of the more common coupling agents. (See Killen and Lindstrom 1984, "Specific killing of lymphocytes that cause experimental Autoimmune Myasthenia Gravis by toxin-acetylcholine receptor conjugates. *Jour. Immun.* 133:1335–2549; Jansen, F. K., H. E. Blythman, D. Carriere P. Pasella, 0. Gros, P. Gros, J. C. Laurent, F. Paolucci, B. Pau, P. Poncelet, G. Richer, H.

Vidal, and G. A. Voisin. 1982. Immunotoxins: Hybrid molecules combining high specificity and potent cytotoxicity. *Immunological Reviews* 62:185–216; and Vitetta et al., supra).

The resultant fusion proteins can be expressed by way of a vector containing a DNA segment encoding the exogenously introduced WIN-ZIP coiled-coil heterodimerization domain.

These can include vectors, liposomes, naked DNA, adjuvant-assisted DNA, gene gun, catheters, etc. Vectors include chemical conjugates such as described in WO 93/04701, which has targeting moiety (e.g., a ligand to a cellular surface receptor), and a nucleic acid binding moiety (e.g., polylysine), viral vector (e.g., a DNA or RNA viral vector), fusion proteins such as described in PCT/US 95/02140 (WO 95/22618) which is a fusion protein containing a target moiety (e.g., an antibody specific for a target cell) and a nucleic acid binding moiety (e.g., a protamine), plasmids, phage, etc. The vectors can be chromosomal, nonchromosomal or synthetic.

Vectors include, but are not limited to, viral vectors, fusion proteins and chemical conjugates. One can use these fusion proteins to examine the effect of their interactions in in vivo systems. Thus, vectors can be selected depending upon the cells where the interaction is being examined.

The vector can be employed to target essentially any desired target cell, such as a glioma. For example, stereotoxic injection can be used to direct the vectors (e.g., adenovirus, HSV) to a desired location. A method based on bulk flow, termed convection, has also proven effective at delivering large molecules to extended areas of the brain and may be useful in delivering the vector to the target cell (Bobo et al., *Proc. Natl. Acad. Sci. USA* 91:2076–2080 (1994); Morrison et al., *Am. J. Physiol* 266:292–305 (1994)). Other methods that can be used include catheters, intravenous, parenteral, intraperitoneal and subcutaneous injection, and oral or other known routes of administration.

Preferably one transiently transfects the cells by known means such as described by Dean, et al., *Proc. Natl. Acad. Sci. USA* 90:8392–96 (1993). Preferably, one would transfect the cells in bulk.

Alternatively, the gene encoding the fusion protein containing the coiled-coil heterodimerization domain can be cloned into a retroviral vector such as the LNCX MuLV shuttle vector under the control of the CMVIE promoter (A. Miller, Central Topics in Microbiology and Immunology, 158 (1991)). The vectors (10 μg) can be transfected by calcium phosphate into a ecotropic cell line such as PE501 ($10^6$ cells/100 mm dishes) (A. Miller, Central Topics in Microbiology and Immunology, 158 (1991)). One can transfect the cells with one of the fusion proteins and then transfect the cell lines with the other fusion protein or co-transfect the cells with both proteins. With certain vectors such as herpes virus, HIV, pox virus, the cell can encode both fusion proteins in the same vector.

Typically when one is using a library one first transfects the cells with the gene encoding the known protein. Thereafter, the bulk cells with the property of interest are selected or wells containing the transfected cells are transfected by different proteins from the library. When one is testing a specific protein pair, one preferably co-transfects the cells or uses a single vector expressing both proteins.

Also encompassed by the present invention are transgenic animals having a gene sequence comprising a WIN-ZIP coiled-coil heterodimerization domain. The WIN-ZIP gene fusion results in a change in a measurable physiological parameter, one can test different binding partners, such as a corresponding WIN-ZIP fusion in different tissues, and at different times, to determine if the parameter can be changed back towards stasis. For example, a mouse may comprise a WIN-ZIP fusion of Src lacking its SH2 domain. In particular backgrounds, one or more of these mice might express a measurable change in phenotype over wild type. One could test the effect of expression of different potential substrates (as a WIN-ZIP fusion) at particular times in particular tissues to see if rescue of the phenotype could be effectuated.

EXAMPLES

Human 293T cells were cotransfected with p54 SAPKβ (JNK3) fused to the WIN-ZIP B1 leucine zipper and Myc tag, along with increasing amounts of v-Src fused at the N-terninus with HA tag plus WIN-ZIP A1 leucine zipper, or HA tag alone. Whole cell lysates or anti-Myc immunoprecipitates were probed with anti-HA or anti-Myc, or anti-PTyr to detect tyrosine-phosphorylated p54.

Figure 3B:
Figure 3C:
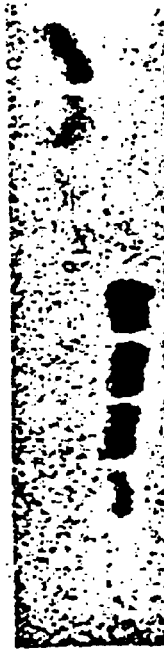

Coiled-coil mediated heterodimerization was seen to induce specific phosphorylation of the tagged substrate by Src tyrosine kinase. As seen in the comparison of the gels of FIG. 3A (whole cell lysates probed with anti-HA) to FIG. 3B (anti-Myc immunoprecipitates probed with anti-Myc) and FIG. 3C (anti-Myc immunoprecipitates probed with anti-Ptyr), p54 is phosphorylated on tyrosine only when the WIN-ZIP A1-Src fusion is present. Normally p54 and Src would not be expected to interact, and p54 is not a known or suspected Src substrate.

All references described herein are incorporated herein by reference.

What is claimed:

1. An assay for determining the activity of a protein—protein interaction comprising a) transforming a cell with a first vector containing a gene encoding a fusion protein comprising a protein containing a modular protein binding domain MPBD and an exogenously introduced a first coiled-coil dimerization which comprises a WIN-ZIP-A1 synthetic amphipathic helix and with a second vector containing a gene encoding a second fusion protein comprising a binding site for the MPBD and an exogenously introduced second coiled-coil dimerization domain interactive with the first dimerization domain, which comprises a WIN-ZIP-B1 synthetic amphipathic helix, b) culturing the transformed cell, c) comparing the activity to a base line control, d) detecting and measuring changes in activity for determining th activity of the protein—protein interaction, wherein the MPBD domain consists of src homology 3 ($SH_3$) and wherein the protein containing the modular protein binding domain (MPBD), which contains a WIN-ZIP-A1 helix is a tyrosine kinase.

2. The assay of claim 1 wherein the base line control constitutes at least two cells wherein each of said cells is transformed by one of the two vectors and not the other.

* * * * *

SEQUENCE LISTING

```
<160> NUMBER OF SEQ ID NOS: 2

<210> SEQ ID NO 1
<211> LENGTH: 156
<212> TYPE: DNA
<213> ORGANISM: Artificial Sequence
<220> FEATURE:
<223> OTHER INFORMATION: Kozak translation start site, followed by an
      HA-epitope, followed by WIN-ZIP-A1 synthetic amphiphatic helix,
      followed by an inframe Bam HI cloning sit

<400> SEQUENCE: 1
accatgtacc catacgatgt tccggattac gctggatcta ccatgactgt ggcgcaactg     60
```

```
gaggaaaagg tgaaaaccct tcgtgctcag aattatgaac ttaagtctcg tgtgcagcgc    120
ttgcgtgagc aggttgccca gcttggagga ggatcc                             156

<210> SEQ ID NO 2
<211> LENGTH: 165
<212> TYPE: DNA
<213> ORGANISM: Artificial Sequence
<220> FEATURE:
<223> OTHER INFORMATION: Kozak translation start site, follwed by a
      Myc-epitope, followed by a WIN-ZIP-B1 synthetic amphipathic helix,
      followed by an in-frame BamHI cloning sit

<400> SEQUENCE: 2
accatggagc aaaagctcat ttctgaagag gacttgaatg aaggatctac catgtccgtt    60
gacgaactgc aggctgaggt tgaccagctg caggacgaga attacgctct gaagaccaag   120
gttgcgcagc tgcgtaaaaa ggtggaaaag ctgggaggag gatcc                   165
```